United States Patent [19]

Konikoff

[11] 4,142,521
[45] Mar. 6, 1979

[54] ELECTROSTATIC SOFT TISSUE WOUND REPAIR ENHANCEMENT

[75] Inventor: John J. Konikoff, Short Hills, N.J.

[73] Assignee: Hoffmann-La Roche Inc., Nutley, N.J.

[21] Appl. No.: 754,060

[22] Filed: Dec. 23, 1976

[51] Int. Cl.² .............................................. A61N 1/10
[52] U.S. Cl. ................................. 128/82.1; 128/411; 128/418; 307/88 ET
[58] Field of Search ................. 128/1.3–1.5, 128/82.1, 172.1, 362, 419 F, 419 R, 404, 410, 411, 418; 307/88 ET

[56] References Cited

U.S. PATENT DOCUMENTS

| 3,596,657 | 8/1971 | Eidus | 128/82.1 X |
|---|---|---|---|
| 3,890,953 | 6/1975 | Kraus et al. | 128/1.5 |
| 3,893,462 | 7/1975 | Manning | 128/1.5 X |
| 3,918,459 | 11/1975 | Horn | 128/419 R |
| 3,921,620 | 11/1975 | Nakayama | 128/1.3 |
| 3,929,131 | 12/1975 | Hardwick | 128/82.1 X |
| 3,968,790 | 7/1976 | Fukada et al. | 128/82.1 |
| 3,998,916 | 12/1976 | Turnhout | 264/22 |

FOREIGN PATENT DOCUMENTS

| 2506227 | 8/1976 | Fed. Rep. of Germany | 128/1.3 |
|---|---|---|---|
| 2514561 | 10/1976 | Fed. Rep. of Germany | 128/419 R |
| 1027350 | 2/1953 | France | 128/82.1 |
| 1255797 | 4/1960 | France | 128/441 |
| 2308384 | 11/1976 | France | 128/1.3 |

OTHER PUBLICATIONS

Mascarenhas, "The Electret State . . . Bone", Electrets-Charge, Storage & Transport in Dielectrics, 1973, Electrochemical Society, Inc.
Mascarenhas, "Electret Behavior . . . Walls", Electrets-Charge, Storage . . . Dielectrics, Electrochemical Soc., Inc., 1973.
Murphy et al., "Blood Compatability . . . Electrets", Electrets-. . . Dielectrics, Electrochemical Society, Inc., 1973.

Primary Examiner—Lee S. Cohen
Attorney, Agent, or Firm—Jon S. Saxe; George M. Gould

[57] ABSTRACT

Electrostatic soft tissue wound repair enhancement is provided by means of a self-contained, non-invasively applied bandage arrangement comprising one or more electret elements each providing a small electrostatic field to the particular wound area. The self-contained, wafer-thin bandage may take the form of a sterile, disposable self-adhering band-aid like structure, a surgical sponge or a closely fitting article of clothing.

19 Claims, 6 Drawing Figures

ELECTROSTATIC SOFT TISSUE WOUND REPAIR ENHANCEMENT

BACKGROUND OF THE INVENTION

This invention relates to the enhancement of soft tissue wound repair by the application of weak electrostatic fields provided by one or more electret-type devices, and more particularly to a truly self-contained, yet wafer-thin, disposable bandage arrangement for application at the site of a soft tissue wound for enhancing the healing process. As used herein the word "wound" is intended to include: surgical incisions, abrasions, cuts, punctures, blemishes, tears, sores, blisters, burns, contusions, tissue ruptures and the like.

Over the last decade several reported studies have been conducted with the objective to demonstrate that the application of small electrical currents (in the micro ampere range) or weak magnetic or electrical fields would effect the growth or reunion of bone or enhance the repair of soft tissue (e.g. skin). While most of these have reported successes, it remains unclear even to the present time as to exactly why such applications have the effects that they do.

Representative of the successful techniques and systems for the repair of bone fracture or bone nonunion is the article of Z. B. Friedenberg et al, "Healing of Nonunion of the Metal Malleolus by Means of Direct Current: a Case Report", Journal of Trauma, 11, 883–885 (1971). Typically, a system representative of this work on bone structure is comprised of a special designed (constant) current circuit, usually battery powered, and containing two electrodes. The cathode is usually placed at one side of the fracture (situs), passing completely through the bone, and the anode on another portion of the bone or at a site distant from the fracture in or on the soft tissue. Application, of course, is via surgery. Customarily, the limb is then casted with the electronics strapped or taped to the cast.

From the work of Friedenberg, and others who have followed his general technique, an improved approach in the area of bone fracture repair has evolved which utilizes electromagnetic fields in a basically noninvasive technique. Such a technique is described, for example, in the article of C. A. L. Bassett et al., "Acceleration of fracture repair by electromagnetic fields. A surgically noninvasive method", Annals of the New York Academy of Science, 238, 242–262, 1974. In Bassett, for example, there is disclosed a system involving pulsed low frequency electromagnetic waves of low intensity being applied across a bone fracture site to induce voltages of a magnitude generally comparable to that produced by deformation (somewhat akin to piezoelectric response in bone distress). In this particular arrangement there is effected essentially a simulation of the natural piezoelectric generation of electricity in bone to accelerate the natural healing process in the bone. Such arrangements usually call for battery powered circuitry to provide the pulsed electromagnetic energy, which is applied to the situs through a pair of electrodes. In this improved technique, however, such electrodes usually take the form of relatively cumbersome plate-shaped electrodes placed on the skin overlying the bone to be treated.

The systems and techniques of the prior art as represented, for example, by Friedenberg and Bassett, are, of course, directed to bone structure as opposed to soft tissue. Such systems require for the most part, specially designed circuitry and associated electrodes which in at least some of the arrangements, are required to be surgically implanted. Such arrangements, moreover, require some form of power pack, usually employing batteries, which nevertheless, must be strapped or taped to the patient, and at the very least is bulky, clumsy and relatively heavy, and likely to impair the freedom of movement of the patient. Some of these prior art arrangements, further, require the generation of electric currents actually through the bone or the application of relatively high voltages (e.g. 24 volts), as to either or both of which patient safety may also be a factor. It may be generally said of such arrangements that there is required to be effected the active or dynamic generation or inducement of electrical currents or voltages in the body structure under treatment.

It is also known from U.S. Pat. No. 3,968,790 to Fukada et al. (The work of Fukada et al. is also found in Japan, J. Appl. Phys. Vol. 14, No. 12, [1975] "Callus Formation by Electret"), to surgically place in physical contact with or around a particular bone structure an electret type device for effecting callus formation and/or wound (i.e. fracture) repair. The Fukada work, however, is also limited to operation in connection with bone structure, utilizing an invasive technique for the application of an electret on or around the bone structure. It is, moreover, primarily concerned with callus formation on bone as opposed, for example, to the promotion of healing.

Another technique and apparatus for aiding formation of bone forming material is described in U.S. Pat. No. 3,745,995 to Kraus. The general technique covered therein involves invasive application of the disclosed structure on the bone itself. Intended is a splinting type arrangement involving partially noninvasively-applied structure. This latter-mentioned embodiment is rather bulky, however, being comprised of a pickup coil and a pair of electrodes straddling a region of the bone structure where callus formation is desired. Active field generation means are required for inducing in the pickup coil an AC current so as to induce alternating currents or potentials between the electrodes, which electrodes actually are embedded in the bone itself.

There have also been proposed systems and techniques aimed at treating soft tissue injuries, wherein the heating process is enhanced through the application of AC or DC currents right through and proximate the wound site. Such techniques are normally non-invasive and are represented, for example, by the work of D. Assimacopoulos, "Wound healing promotion by the use of negative electric current", American Surgeon, 34,423–431 (1968); L. E. Wolcott et al. "Accelerated healing of skin ulcers by electrotherapy: preliminary clinical results", Southern Medical Journal, 62,795–801 (1969); and J. J. Konikoff, "Electrical Promotion of Soft Tissue Repairs" Annals of Biomedical Engineering, 4,1–5, (1976). Common to such techniques in the direct application of a constant current output from an electronic circuit through an electrode attached to the site of lesion or repair and a second electrode, usually of the same material, located at a distance on or through the skin of the same organism. Such circuitry and devices are powered either by battery or through a converter from regular AC line current.

Such soft tissue-related techniques and systems possess many of the drawbacks of the bone structure-related systems and techniques, in that, for example, relatively, heavy clumsy and bulky supplies are required to provide the active generation of electrical current in and at the site of tissue repair. Also, electrodes are required to be attached or implanted to effect the path of current flow through the wound site. Moreover, while such arrangements, like those dealing with bone, tend to restrict the freedom of the patient, they are also generally undesirable from the standpoint of treating a patient on an out-patient basis or indeed in self-treatment instances.

In spite of the fact that the prior art makes use of electric fields to enhance bore fracture or directly applied electrical current to enhance and repair soft tissue, the prior art approach generally requires apparatus which is unwieldy or involves surgical invasive techniques. As such, ambulatory patients are indeed restricted during treatment; also, in many instances relatively minor wounds cannot be properly treated primarily because the patient is not confined to bed. Additionally, in those instances where batteries or battery packs are utilized, they must be replaced or recharged from time to time, which necessarily increases the total cost of treatment. Naturally, also, the potential for infection is ever present in those techniques and arrangements of the prior art requiring invasive surgery.

In addition to the need to overcome the drawbacks of the prior art, it would additionally be most desirable to provide a means and technique for soft tissue wound repair enhancement which allows for complete freedom of movement of the patient by means of a light-weight, wafer-thin, preferably self-adhering, self-contained, sterilized, disposable, statically-operable device, not having to be precisely fixed geometrically in relation to the wound site, and which may be shaped, tapered or cut relative to the wound area configuration itself.

SUMMARY OF THE INVENTION

It is, therefore, the principle object of this invention to overcome the aforementioned drawbacks of the prior art and also provide the above-indicated desirable features, particularly in regard to soft tissue repair.

The principle objective of this invention is accomplished, and the approach of soft tissue wound repair enhancement made more universally applicable, by a device providing a self-contained electrostatic field for aplication directly to damaged tissue at virtually any anatomical site.

According to the broader aspects of the invention, there is provided a method for promoting soft tissue wound healing comprising applying non-invasively and in close proximity to a soft tissue wound site of an organizm an electret providing an electrostatic field to the wound site.

Also according to the invention there is provided apparatus for enhancing the natural healing process of a soft tissue injury of an organism comprising a base intended for placement upon a portion of the organisms's anatomy which has sustained a soft tissue injury and including means for securing the base to the organism, and electret means mounted on said base for non-invasive placement proximate the injury for providing an electrostatic field at the injury location.

The device of the invention is particularly characterized by incorporating the electret into a self-sticking (adhesive) bandage or a surgical type sponge. Such a device enables a long-term electrostatic field source to be conveniently available for the soft tissue repair procedure, and is in sterilizable, disposable form.

By the invention, the electret element replaces and makes obsolete the need for batteries, electronic circuits, encapsulating material etc. The invention further obviates the need for any surgery or implantation of any electrodes, and the like, by providing, rather, the application of an electret-fitted, self-adhering bandage enabling simple and effective treatment in the form of soft tissue wound repair enhancement. The electret device provides an electrostatic field, as opposed, for example, to the dynamic application of current or voltage or dynamic current or voltage inducements in and at the tissue situs under treatment. Moreover, the invention provides for complete freedom of movement of the patient through the approach of providing a sterile, disposable, wafer-thin "Band-aid" type bandage, which, of course, may take the form of (or be part of) a surgical sponge, a mitten, a sock, an arm brace or band, or indeed even a cast. In is, in fact, within the scope of this invention that such a device take the form or be part of a tubular chest neck, arm or leg sleeve.

The invention has particular application in the field of dermatology, for example, treatment of the skin following punch biopsy for dermatological reasons. Moreover, it is applicable in the treatment of disuse osteoporosis, such as may come about through prolonged immobilization or a prolonged tenure out in space. A particular related application of the invention would be in the area of bed sores healing or prevention, for example, treatment of decubital ulcers using electret-modified, cotton surgical sponges.

In particular regard to applications of the invention in post-surgical situations, it is important in such situations to ensure that the incision through the skin joins together as quickly as possible, so that the infection potential as well as the probability of incision reopening is decreased. This is best accomplished by increasing strength at the incision, which heretofore has been effected by suturing or clamping. However, by increasing the rate of healing, the same desirable end point is achieved-the edges of the incision grow together faster, thus closing the wound more quickly and increasing the strength at that site. Such may be achieved by applying a device according to the invention in the form of a surgical-type sponge (self adhering or otherwise), wherein the electrostatic field applied to the surgical site results in the desired increased healing rate.

Since most surgical incisions are too long to be treated by available plastic type strip bandages, the form of the invention in a surgical sponge arrangement would be preferable in such instances. Thus, for example, by preparing the electret(s) arrangement in a specific geometry to fit a typical surgical sponge geometry (which may be square, rectangular, circular, oval etc.) and placing it within (e.g. between the layers of gauze comprising) the sponge, the entire device may then be placed over the surgical incision in customary manner; that is, adhesive tape or any other form of gummed material (tape) may be used to hold the sponge in place. Should the incision be longer than perhaps four inches (which may be an appropriate maximum size of sponge), then a series of sponges each containing one or more electret devices may be placed one after the other over the incision. Alternatively, it is envisioned that the electret-loaded sponge material may be manufactured in endless form, made available in a roll, which would enable one to apply a sponge piece of any desirable length.

This type of sponge-electret arrangement would be particularly applicable in reference to the above-mentioned enhancement of remission and healing of decubital ulcers (pressure sores) caused by prolonged pressure on the skin of for example a bedridden subject.

BRIEF DESCRIPTION OF THE DRAWINGS

The above-mentioned and other objects and features of the invention will be better understood by reference to the following detailed description taken in conjunction with the accompanied drawings, in which.

DESCRIPTION OF THE PREFERRED EMBODIMENT

Figure 1A:
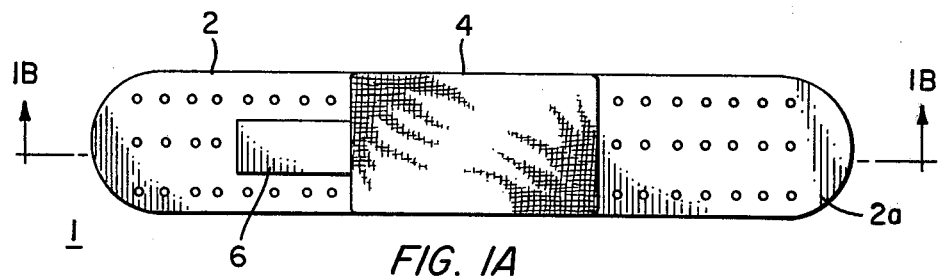
FIGS. 1A and 1B illustrate in underside and side views respectively a self-adhering bandage strip constructed in accordance with the invention.

Essentially, the invention concerns the enhancement of soft tissue wound repair utilizing an electrostatic field derived from an electret to promote the healing. Preferably the electret is located in the gauze portion of a bandage, for example, an adhesive plastic strip having the gauze portion mounted thereon.

An electret is a permanently polarized piece of dielectric material. Such a device may be produced by subjecting the dielectric material to a strong electric potential difference. It is the electrical analogy of a permanent magnet. Many common materials may be made into electrets, including teflon, mylar, carnauba and other organic waxes and polymers. Those electrets made of, for example, mylar, teflon and other polymers are flexible devices which can readily assume the shape of the object surface to which they are applied.

Several techniques are available for the manufacture of electrets. The classical method of making electrets with dielectric material, at least from the laboratory point of view, employs the application of an electric field to the sample while it is heated and successively cooled to room temperature, i.e. the so called thermomethod. This process results in the injection of space charges into the dielectric (e.g. carnauba wax) and in a dipole alignment, or microscopic charge separation. These charges have been termed homo-and hetero-charges, respectively, because of the polarity of the space charges and dipoles relative to the polarity of the electrodes. The effective surface charge is generally the difference of the homo- and hetero-charges. Unfortunately, these classical wax electrets have charge-decay characteristics that are not suitable for long-term application. This is because the homo-charges and the hetero-charges, which are both present, have different decay times, often leading to decays characterized by an apparent change of the polarity of the electret.

Polymers suitable for use as electret material are, however, mostly nonpolar substances capable of storing only space charges in traps, and, consequently, essentially permanently-charged electrets can be made using these materials.

A second methodological category for the production of electrets using dielectric materials (polymer foils 2-25 $\mu$m thick) is the electron bombardment technique which uses penetrating beams (range of electrons greater than the thickness of the polymer material), as well as the nonpenetrating beams. These methods are capable of producing high initial-charge densities on foil electrets. The technique of charge injection by electron beams is capable of considerable control. A set-up consists of: a modified electron-beam accelerator having an RF source and a source magnet, a diffusion pump, proper lens, shutoff valves, scan plates for vertical and horizontal alignment, and a sample holder to hold the metal-coated material. Beam energies of 20 kev with beam currents of 0.1 $\mu$a at exposure times of 1 sec are normal for charging a 25 $\mu$m foil.

In another particular construction, an electret may take the form of, for example, a 1.0 mil thick teflon polymer having vapor-deposited on one side thereof a 0.7 mil layer of aluminum. The charging of the polymer may be accomplished by the technique known as "breakdown fields", wherein a large electromotive force (say 10 KV) is impressed on the metal side of the polymer foil via a pair of suitable electrodes. The polymer with its metalized surface up is supported on a dielectric base of proper conductivity (for example a 0.5 cm soda lime glass face) that is resting on the one (lower) electrode. Following a charging time ranging from say ten to thirty minutes, the EMF is turned off, the upper electrode removed and the charged polymer (electret) is removed after being grounded to the base electrode. Field strengths of about $-2.0 \times 10^{-9}$ coulombs/cm$^2$ are easily attainable on the polymer side of the electret as a result of this treatment. Such a field strength is quite small, and comparable to the electrostatic field (ESP) generated in a comb after it passes through one's hair. Such field strengths are quite innocuous from the standpoint that they exhibit no detrimental effects in man or animal, irrespective of the time of exposure. Thus, patient safety is assured.

Formerly, electrets have been known to "short out" temporarily in the presence of a liquid. It is for this reason that means have been provided heretofore to insulate the electret to prevent direct contact with a liquid such as from an oozing wound. Of late, however, a technique has been developed to seat the electret charge, thus avoiding this problem. See in this regard, for example, the article by B. Gross et al. "Heat Sealing of Teflon Electrets by Annealing", Jour. App. Phys., Vol. 46 No. 11, Pp. 4674–7), Nov. 1975.

For a more complete understanding of the electret device itself and the techniques for making same, the reader is referred in particular to the above-mentioned Fukada patent and the references cited therein, as well as the articles of: G. M. Sessler et al., "Production of High Quasi-Permanent Charge Densities on Polymer Foils by Application of Breakdown Fields", J. Appl. Physics, 43: pgs 922–26, 1972; and (2) G. M. Sessler et al., "Research in Polymer Electrets", Photographic Science and Engineering, Second Internat'l. Conference on Electrophotography pp 162–66, 1974.

In particular reference to FIG. 1 there is illustrated a device applied according to the invention to a soft tissue surface area 1 of an organism. The device is comprised of a base 2 of gummed tape or adhesive-coated plastic material, such as may be found in the so-called "Band-aid" type bandage arrangements commercially available. One or more electret devices 3 are suitably secured to the base 2 on the gummed or adhesive side 2a. Suitably formed over, and preferably about, each electret element is a gauze structure 4, such as one or more gauze pads of conventional construction intended to make direct contact with the tissue surface 1a of the organism at or near the wound site 1b.

Figure 1B:
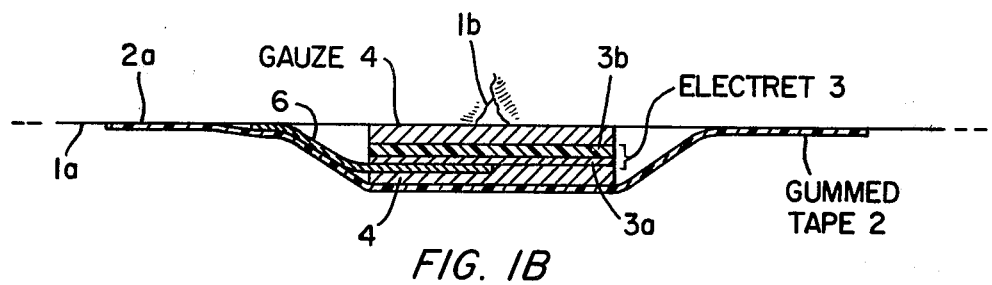

With a proper application of the arrangement depicted in FIGS. 1A and 1B, the electret element 3 is placed securely in close proximity to the wound site, thus providing at the wound site a self-contained electrostatic stimulus, an electrostatic field borne by a wafer-thin substrate 3b to enhance wound repair, while allowing the patient complete freedom of movement and activity and which is free of electrical and other possible dangers to the patient's safety. In the arrangement according to FIG. 1B, there is illustrated a ground strip 6 electrically connected to the electret 3, which ground is intended to be in contact with the skin to "complete the circuit". Specifically, the attached end of the ground strip 6 is secured to the aluminum-coated face 3a of the electret element (i.e. the face away from the wound site).

Figure 2A:
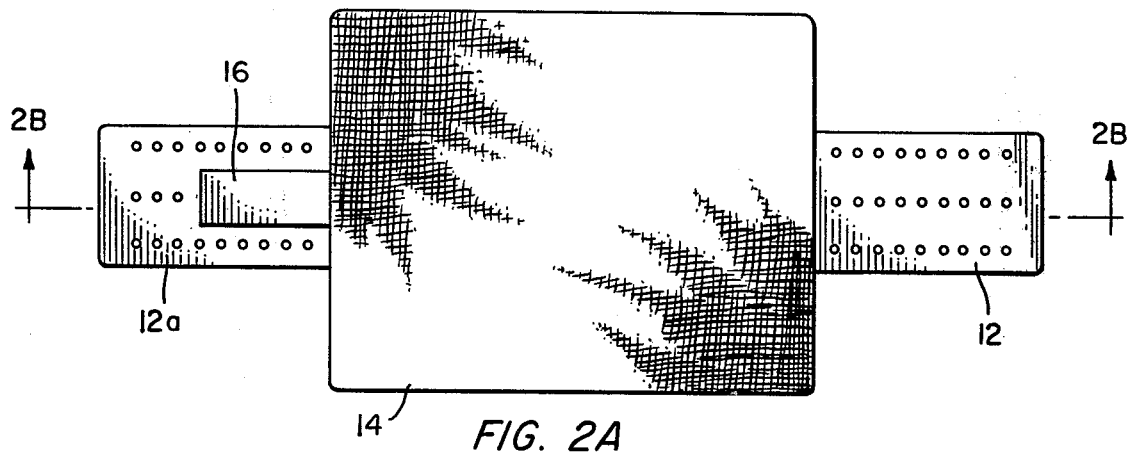
FIGS. 2A and 2B illustrate also in underside and side views respectively another embodiment constructed in accordance with the invention, this time taking the form of a surgical-type sponge arrangement.
Figure 2B:
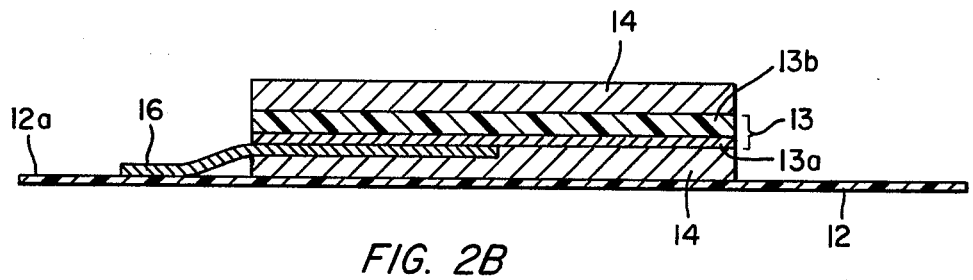

Another arrangement constructed in accordance with the invention is depicted in FIGS. 2A and 2B. In the embodiment there is suitably secured upon a gummed tape or plastic adhesive base 12 one or more electrets of larger size 13 for accommodating the larger wound sites, such as may come about from surgery. Such electret elements 13 are also provided with the grounding strip 16 in electrical contact with the aluminized electret surface 13a, again in order to make contact with the skin to complete the circuit. Suitably mounted atop the electret element(s) 13 is a correspondingly enlarged gauze arrangement 14, which may take the form of a suitably shaped surgical sponge. Preferably, the electret element 13 may be placed within the sponge structure 14 itself. Such an arrangement as is depicted in FIGS. 2A and 2B is particularly suitable for the treatment of decubitus ulcers and other large surface injuries. In both FIGS. 1B and 2B, thickness has been exaggerated for clarity.

In use, the device is placed over the cut, incision, ulcer or other skin wound with the gauze portion 14 in contact with the injured part. Depending on the moisture content of the wound and its location, the electrified bandage may be changed as often as necessary, simply because it is entirely disposable.

The field strength of the electret will remain essentially constant for several months or even years, so that the original bandage containing the electret can be left in place for relatively long periods of time. Such may be necessary particularly for stubborn repair situations which nevertheless due to other circumstances dictate or require prolonged or uninterrupted application of the device.

Figure 3A:
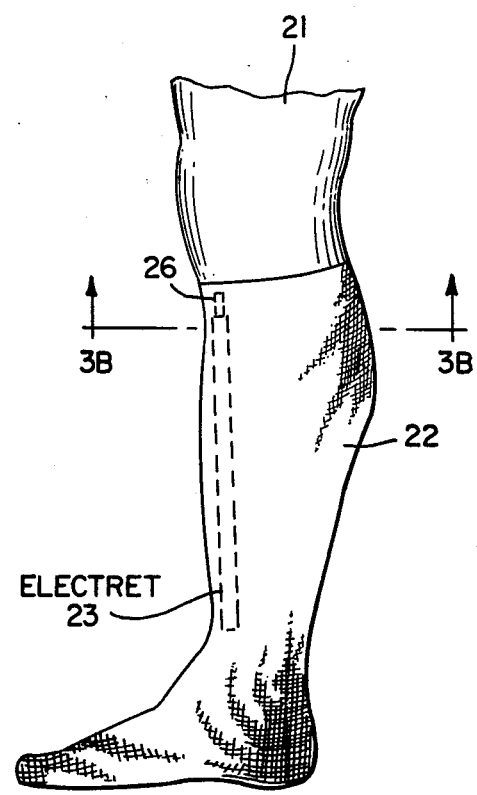
FIGS. 3A and 3B illustrate yet another embodiment of the invention taking the form of an article of clothing, in particular a stocking.
Figure 3B:
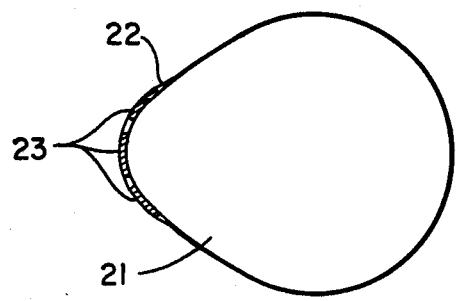

Yet another embodiment of the invention is illustrated in FIGS. 3A and 3B, wherein there is is shown the base portion 22 now taking the form of a stocking or sock. It just as easily may take the form of a mitten or glove or a tight fitting collar or sleeve, such as a tubular chest sleeve. In such an arrangement as is depicted in FIGS. 3A and 3B there may be included in, or affixed to the under surface of, the base 22 one or more (preferably a series) of wafer-thin, polymer (or other type) electret strips 23 having grounding strips 26. Alternately, these electret strips may be selectively mountable to the to the inner surface thus enabling same to be situated in a more precise location with respect to the area of treatment. The electret strips 23 are situated when the article of clothing is in place, to press firmly against the treatment area (in the example here depicted, the tibia) when the stocking is drawn up over the leg 21.

The abilities and operability of the invention have been demonstrated in recent studies by and under the direction of the inventor on the promotion of soft tissue wound repair. The apparatus utilized in these particular studies has taken the form of an electret mounted on a plastic strip bandage, substantially like that shown in FIGS. 1A and 1B.

In one such study, under sterile conditions, each of several anesthetized New Zealand white male and female rabbits (1.5–2.0 kg each) were incised bilaterally 2 cm on either side of the spine in the lumbar region. The incisions were of full skin thickness, 2 cm long. They were closed using three interrupted sutures, silk 000 and a plastic strip was placed over each incision. On one side an experimental strip, i.e. one containing an electret, was placed. On the other side was placed a standard non-modified plastic strip or a strip modified with a non-electrified piece of dielectric material, duplicating in geometry and appearance the electret. In this manner, each animal served as its own control with the treated side being compared with either an unaltered plastic strip or a null-field modified strip. The placement of the strips was blinded.

Following a seventy-two hour period, the animals were scarified and sections of the skin containing the incisions excised. The sutures were removed and the samples pull-tested using commerical instrumentation, in particular an Instron Tester, Model 1122 at a crosshead speed of approximately 200mm/min. The testing was also done blinded.

The results of the pull-testing are presented below. In this Table the loads required to rupture the incisions have been reduced to units of $g/mm^2$.

| Animal No. | Load to Rupture, $g/mm^2$ | |
|---|---|---|
| | Control | Treated |
| 1 | 52.1 | 82.5 |
| 2 | 9.1 | 13.7 |
| 3 | 6.9 | 6.9 |
| 4 | 1.7 | 8.9 |
| 5 | 20.0 | 24.2 |
| 6 | 3.7 | 19.7 |
| 7 | 3.6 | 9.8 |
| Mean Values | 13.9 | 23.7 |

The ratio of the mean values of the treated and control loads to rupture is 1.71, indicating an increase of over 70% in wound strength for the treated incisions.

Of the measured electrostatic voltage readings for the electret apparatus employed in the treated cases, the average field strength is about $-1.9 \times 10^{-9}$ coulombs/$cm^2$.

What is claimed is:

1. A method for promoting soft tissue wound healing comprising applying non-invasively and in close proximity to a soft tissue wound site of an organism an electret providing an electrostatic field to the wound site.

2. Method according to claim 1 further including mounting said electret to the adhesive-covered side of an adhesive bandage, wherein the applying step comprises applying said electret in close proximity by placing said adhesive-covered side of the bandage onto the organism.

3. Method according to claim 2 further including mounting a piece of gauze about said electret, and wherein the adhesive bandage assembly is sterile.

4. Method according to claim 3 wherein said bandage assembly is disposable.

5. Method according to claim 1 further including mounting at least one electret in an article of clothing intended to be worn on the hand of a patient wherein said at least one electret is proximate of a hand injury site wherein the applying step comprises applying said electret in close proximity by placing said article of clothing onto the organism.

6. Method according to claim 1 further including mounting at least one electret in an article of clothing intended to be worn on the lower leg area of a patient wherein said at least one electret is located proximate a lower leg injury site, wherein the applying step comprises applying said electret in close proximity by placing said article of clothing onto the organism.

7. Method according to claim 6 wherein said article of clothing is a stocking and wherein one or more electrets are mounted on the inner surface thereof for placement closely proximate the location of a lower leg injury.

8. Method according to claim 1 further including mounting at least one electret in a neck collar arrangement wherein said at least one electret is located proximate a neck injury site, wherein the applying step comprises applying said electret in close proximity by placing said neck collar arrangement onto the organism.

9. Method according to claim 1 wherein said electret is predeterminally mounted in a cast arranged on an extremity of a patient so as to be proximate the intended soft tissue injury site, wherein said applying step comprises applying said electret in close proximity by placing said cast onto the organism.

10. Method according to claim 1 further including shaping a base to the portion of the body of the organism bearing the wound, shaping the electret to correspond to said base and mounting the electret to the base, wherein the applying step comprises applying said electret in close proximity by placing said base onto the organism.

11. Method according to claim 1 further including shaping the electret to conform to the wound site.

12. Apparatus for enhancing the natural healing process of a soft tissue injury of an organism comprising a base intended for placement upon a portion of the organism's anatomy which has sustained a soft tissue injury and including means for securing the base to the organism, and electret means, mountable on said base, mounted to said base for non-invasive placement proximate the injury for providing an electrostatic field at the injury location.

13. Apparatus according to claim 12 further including a piece of gauze material mounted about said electret means.

14. Apparatus according to claim 12 wherein said securing means is comprised of an adhesive coating on one side of said base to form a self-contained, self-adhering bandage.

15. Apparatus according to claim 12 wherein said base is a closely fitting article of clothing.

16. Apparatus according to claim 12 wherein said base is a cast adapted to be arranged on an extremity of the organism.

17. Apparatus according to claim 12 wherein said electret means is configured to conform to the geometry and location of the injury.

18. Apparatus according to claim 17 wherein said electret means includes a plurality of electret elements predeterminably arranged to provide an electrostatic field to virtually the entire injury area.

19. Apparatus according to claim 12 wherein said base constitues a surgical sponge.

* * * * *